United States Patent [19]

Kanekiyo

[11] Patent Number: 4,960,541

[45] Date of Patent: Oct. 2, 1990

[54] AQUEOUS LIQUID DETERGENTS CONTAINING AN N-ACYL-ASPARTATE, AMINE OXIDE AND ALKYL ETHER SULFATE

[75] Inventor: Takazumi Kanekiyo, Mie, Japan

[73] Assignee: Mitsubishi Petrochemical Co., Ltd., Tokyo, Japan

[21] Appl. No.: 400,927

[22] Filed: Aug. 31, 1989

[30] Foreign Application Priority Data

Sep. 30, 1988 [JP] Japan ................................ 63-246095

[51] Int. Cl.[5] .......................... A61K 7/50; C11D 1/10; C11D 1/29; C11D 1/75

[52] U.S. Cl. ..................................... 252/546; 252/173; 252/527; 252/547; 252/551; 252/DIG. 5; 252/DIG. 7; 252/DIG. 13; 252/DIG. 14; 424/70

[58] Field of Search ............... 252/173, 527, 528, 532, 252/546, 547, 551, DIG. 5l, DIG. 7, DIG. 13, DIG. 14; 424/70

[56] References Cited

U.S. PATENT DOCUMENTS

| | | | |
|---|---|---|---|
| 4,009,256 | 2/1977 | Nowak | 424/70 |
| 4,436,653 | 3/1984 | Jacobson | 252/547 |
| 4,438,024 | 3/1984 | Del Greco | 252/545 |
| 4,492,646 | 1/1985 | Welch | 252/528 |
| 4,555,360 | 11/1985 | Bissett | 252/547 |
| 4,578,216 | 3/1986 | Fujii | 252/542 |
| 4,832,872 | 5/1989 | Scandel | 252/547 |
| 4,885,107 | 12/1989 | Wetzel . | |

FOREIGN PATENT DOCUMENTS

| | | | |
|---|---|---|---|
| 39-29444 | 12/1964 | Japan . | |
| 48-5904 | 2/1973 | Japan . | |
| 48-10921 | 4/1973 | Japan | 252/546 |
| 48-33964 | 10/1973 | Japan | 252/546 |
| 50-23682 | 8/1975 | Japan . | |
| 51-92802 | 8/1976 | Japan | 252/546 |
| 51-42603 | 11/1976 | Japan . | |
| 53-46841 | 12/1978 | Japan | 252/546 |
| 56-76500 | 6/1981 | Japan | 252/546 |
| 59-138298 | 8/1984 | Japan | 252/546 |
| 61-141797 | 6/1986 | Japan | 252/DIG. 5 |
| 61-291700 | 12/1986 | Japan | 252/546 |

*Primary Examiner*—Dennis Albrecht
*Attorney, Agent, or Firm*—Oblon, Spivak, McClelland, Maier & Neustadt

[57] ABSTRACT

A liquid detergent composition is disclosed, containing (a) an N-acylaspartic acid or a salt thereof, (b) a tertiary alkylamine oxide and (c) an alkyl ether sulfate, the weight composition of the components (a), (b), and (c) falling within the range indicated by a quadrate formed by four points (90,5,5), (75,20,5), (50,20,30), and (65,5,30) in a triangular coordinate constructed by placing the pure components (a), (b), and (c) at the vertices of a regular triangle. The composition exhibits excellent foamability and detergency while retaining mildness to the skin and substantial fluidity.

4 Claims, 1 Drawing Sheet

AQUEOUS LIQUID DETERGENTS CONTAINING AN N-ACYL-ASPARTATE, AMINE OXIDE AND ALKYL ETHER SULFATE

FIELD OF THE INVENTION

This invention relates to a novel three-component system detergent composition. More particularly, it relates to a liquid detergent composition containing an N-acylaspartic acid or a salt thereof as an amino acid-series anionic surface active agent, a tertiary alkylamine oxide as an amphoteric surface active agent, and an alkyl ether sulfate, which is excellent in foamability, detergency, and mildness to the skin.

BACKGROUND OF THE INVENTION

Anionic surface active agents, such as alkylbenzenesulfonates, have widely been used as main components in dishwashing detergents. From the viewpoint of irritation to the skin, the tendency now is turning toward mild detergents containing alkyl ether sulfates and amphoteric surface active agents as main components. However, alkyl ether sulfates are still unsatisfactory in mildness to the skin, and further improvements have been demanded.

It has been proposed to incorporate an N-acylamino acid salt which is not only mild to the skin but effective to inhibit growth of harmful microorganisms causing skin diseases as disclosed in JP-B-46-4256 and JP-B-39-29444 (the term "JP-B" as used herein means an "examined Japanese patent publication"). However, an aqueous solution of the N-acylamino acid salt per se has low detergent action and it lacks detergency and foamability for cleaning off extremely oily dirt, for example, dishes or hair applied with pomade.

JP-A-48-5904 (the term "JP-A" as used herein means an "unexamined published Japanese patent application") discloses use of an N-aclyglutamate in combination with a tertiary alkylamine oxide to thereby improve detergency and foamability without impairing mildness to the skin. However, it has been proved by the inventor's investigations that the tertiary alkylamine oxide must be used in an amount of at least 2/3 as much as the weight of the N-acylglutamate before one can obtain improved detergency and foamability and that incorporation of the tertiary alkylamine oxide in such a high ratio causes gelation and substantial loss of fluidity.

SUMMARY OF THE INVENTION

One object of this invention is to provide a liquid detergent composition exhibiting excellent foamability and detergency while retaining mildness to the skin and fluidity.

As a result of extensive investigations, the inventor has found that incorporation of an alkyl ether sulfate into a detergent containing an N-acylaspartic acid or a salt thereof and a tertiary alkylamine oxide brings about improvements on foamability and detergency while retaining mildness to the skin and substantial fluidity.

That is, the present invention relates to a liquid detergent composition containing (a) an N-acylaspartic acid or a salt thereof represented by formula (I):

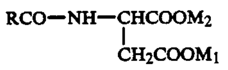

(I)

wherein R represents an alkyl or alkenyl group having from 7 to 21 carbon atoms; and $M_1$ and $M_2$ each represents a hydrogen atom or a cation derived from Na, K, $NH_4$ or an alkanolamine, (b) a tertiary alkylamine oxide represented by formula (II):

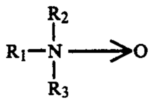

(II)

wherein $R_1$ represents an alkyl or alkenyl group having from 10 to 18 carbon atoms; and $R_2$ and $R_3$ each represents an alkyl group having from 1 to 3 carbon atoms, and (c) an alkyl ether sulfate represented by formula (III):

$$R_4-O+CH_2CH_2O\frac{}{}_{\bar{p}}SO_3M_3 \qquad (III)$$

wherein $R_4$ represents an alkyl or alkenyl group having from 7 to 20 carbon atoms; $\bar{p}$ represents an average number of moles of ethylene oxide added and is selected from an integer of from 1 to 5; and $M_3$ represents a cation derived from Na, K, $NH_4$ or an alkanolamine, the weight composition of the components (a), (b), and (c) falling within the range indicated by a quadrate formed by four points (90,5,5), (75,20,5), (50,20,30), and (65,5,30) in a triangular coordinate constructed by placing the pure components (a), (b), and (c) at the vertices of a regular triangle.

DETAILED DESCRIPTION OF THE INVENTION

Figure 1:
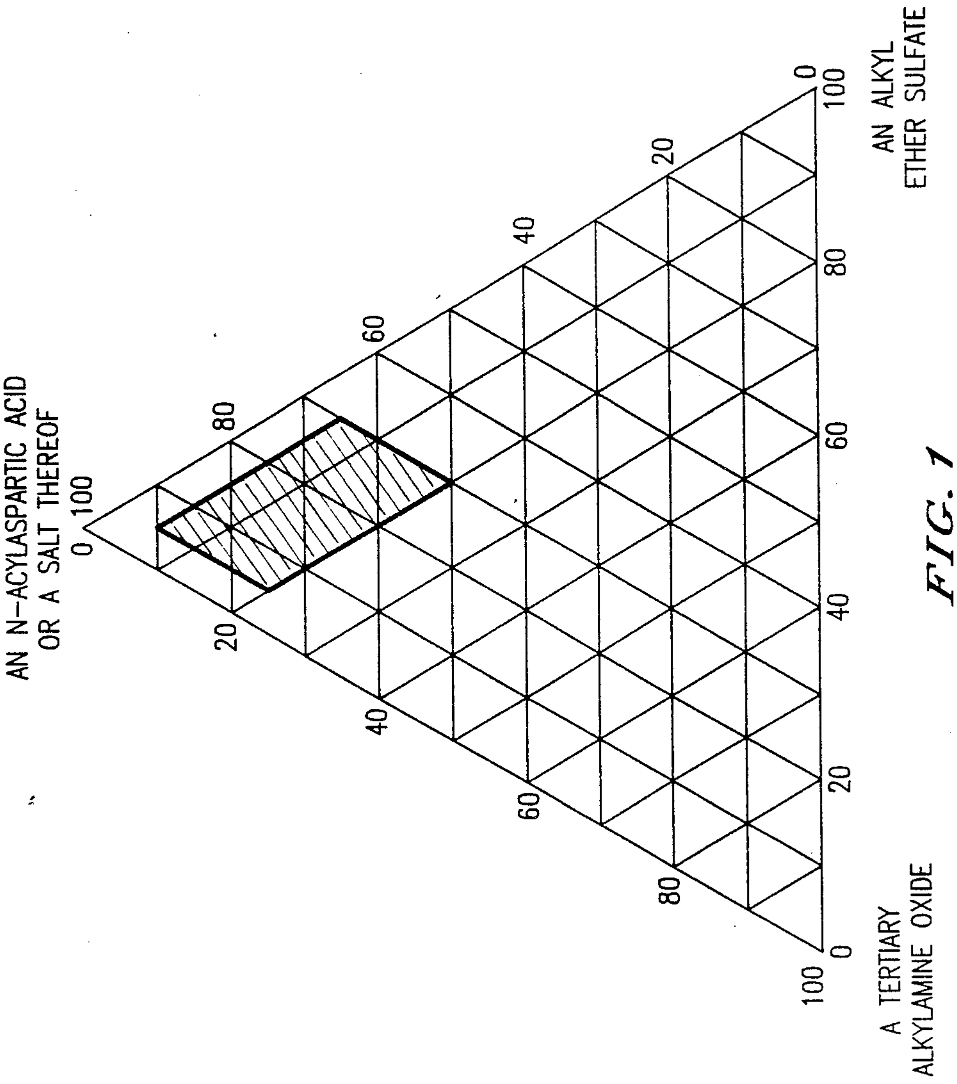
FIG. 1 is a triangular coordinate constructed by placing the pure components (a), (b), and (c) at the vertices, in which a composition of the detergent composition of this invention is indicated by a shaded quadrate.

The N-acylaspartic acid or a salt thereof represented by formula (I) which can be used in the detergent composition of the present invention includes an L-form, a D-form, and a mixture thereof.

Specific examples of the N-acylaspartic acid or a salt thereof which can suitably be used are N-lauroylaspartic acid, N-myristoylaspartic acid, N-palmitoylaspartic acid, N-stearoylaspartic acid, and N-oleoylaspartic acid, and their salts, e.g., sodium salts, potassium salts, monoethanolammonium salts, and triethanolammonium salts.

The tertiary alkylamine oxide which can be used in the detergent composition of the present invention can be obtained, for example, by oxidizing a straight chain or branched long-chain alkyl tertiary amine with an oxidizing agent, such as hydrogen peroxide and Caro's acid.

Examples of suitable tertiary alkylamine oxides are lauryldimethylamine oxide, myristyldimethylamine oxide, cetyldimethylamine oxide, lauryl-2-hydroxyethylamine oxide, laurylmethylethylamine oxide, lauryldiethylamine oxide, myristyldiethylamine oxide, oleyldimethylamine oxide, oleyldiethylamine oxide, myristylethylpropylamine oxide, lauryldipropylamine oxide, myristyldipropylamine oxide, cetyldipropylamine oxide, cetylmethylpropylamine oxide, and cocoalkyldimethylamine oxide.

The alkyl ether sulfate which can be used in the present invention is a sodium, potassium, ammonium or alkanolamine salt of a sulfuric ester obtained by sulfation of an ethylene oxide adduct of a synthetic or naturally-occurring alcohol having from 7 to 20 carbon atoms, for example, with $SO_3$ or chlorosulfonic acid. A specific example of suitable alkyl ether sulfates is the one which is prepared by sulfating an alcohol ethoxylate obtained by addition reaction between 1 mol of "Dobanol 23" (a product of Mitsubishi Petrochemical Co., Ltd.) and 3 mols of ethylene oxide with $SO_3$ gas by means of a falling film type sulfation apparatus and then neutralizing with a sodium hydroxide aqueous solution.

In the liquid detergent composition according to the present invention, the weight composition of (a) the N-acylaspartic acid or a salt thereof, (b) the tertiary alkylamine oxide, and (c) the alkyl ether sulfate should be within a range surrounded by a quadrate formed by lines connecting four points (90,5,5), (75,20,5), (50,20,30), and (65,5,30) in a triangular coordinate constructed by placing the pure components (a), (b), and (c) at the vertices of a regular triangle.

If desired, the detergent composition of this invention may further contain other known components commonly employed in liquid detergent compositions, such as amphoteric surface active agents and nonionic surface active agents in amounts that do not impair the effects of the present invention, and commonly employed additives, such as viscosity-controlling agents, e.g., glycerin, propylene glycol, and inorganic salts; flavors, dyes, ultraviolet absorbents, and antioxidants.

The liquid detergent composition according to the present invention is mild to the skin and exhibits excellent foamability and detergency.

The present invention is now illustrated in greater detail by way of the following Examples, but it should be understood that the present invention is not deemed to be limited thereto.

EXAMPLES 1 TO 10

Sodium N-lauroyl-L-aspartate, lauryldimethylamine oxide, and sodium Dobanol 23 (3Eϕ) sulfate obtained by sulfation of an ethylene oxide (3 mol) adduct of an aliphatic alcohol having 12 and 13 carbon atoms ("Dobanol 23") were mixed with water to prepare a liquid detergent composition having a concentration of each component as shown in Table 1, with the total concentration of these three active components being 20% by weight. The resulting detergent composition was evaluated for foamability, detergency, and viscosity according to the following test methods. The results obtained are shown in table 1.

(1) Foamability

The detergent composition was 200-fold diluted with distilled water. A 20 ml portion of the thus diluted detergent was put in a 100 ml-volume measuring cylinder with a ground-glass stopper together with 1 g of triolein as an oil component. The cylinder was stoppered and given 20 vertical sharp shakings. Immediately after the shaking, the cylinder was placed horizontally, and the volume of the foam was read out.

(2) Detergency

Slide glass was dipped in a model dirt having the following composition for 1 to 2 seconds and then air-dried. The slide glass having adhered thereto the dirt was washed with the liquid detergent composition 200-fold diluted with distilled water (content of surface active agent: 0.1% by weight) at 25° C. for 3 minutes under rotation of 250 rpm and then rinsed with distilled water at 25° C. for 1 minute by means of a Leenerts improved detergency testing machine. The slide glass was air-dried, and the residual oil was determined. A detergency (%) can be calculated from equation:

$$\text{Detergency (\%)} = \frac{Ws - Ww}{Ws} \times 100$$

wherein Ws is the amount of the deposited oily dirt before washing; and Ws is the amount of the oily dirt remaining after washing.

Composition of Model Dirt

| | | |
|---|---|---|
| Soybean oil (JP) | 10 | g |
| Beef tallow (JP) | 10 | g |
| Monoolein | 0.25 | g |
| Oil Red | 0.1 | g |
| Chloroform | 60 | ml |

(3) Viscosity

A viscosity of the detergent composition at 25° C. was determined at a shear rate 1 ($S^{-1}$) by the use of a corn/plate type rotation viscometer ("EHD, EMO, ELD" manufactured by Toki Sangyo K. K.).

COMPARATIVE EXAMPLES 1 TO 10

A liquid detergent composition having a composition shown in Table 2 was prepared. The properties of the resulting detergent composition were evaluated in the same manner as in Examples. In cases where the composition became a slurry or a gel, the viscosity was not determined, and only the appearance was observed. The results obtained are shown in Table 2.

COMPARATIVE EXAMPLES 11 TO 16

A liquid detergent composition having a composition shown in Table 3 was prepared. The properties of the resulting detergent composition were evaluated in the same manner as in Examples, and the results obtained are shown in Table 3.

TABLE 1

| | Example No. | | | | | | | | | |
|---|---|---|---|---|---|---|---|---|---|---|
| | 1 | 2 | 3 | 4 | 5 | 6 | 7 | 8 | 9 | 10 |
| Composition (wt %): | | | | | | | | | | |
| Sodium N-lauroylaspartate | 18 | 17 | 15 | 13 | 12 | 10 | 12 | 14 | 15 | 14 |
| Lauryldimethylamine oxide | 1 | 1 | 1 | 1 | 2 | 4 | 4 | 4 | 4 | 2 |
| Sodium Dobanol 23(3Eϕ) sulfate | 1 | 2 | 4 | 6 | 6 | 6 | 4 | 2 | 1 | 4 |
| Performance Properties: | | | | | | | | | | |
| Foamability (ml) | 80 | 75 | 70 | 65 | 80 | 85 | 90 | 85 | 80 | 75 |
| Detergency (%) | 80 | 78 | 75 | 70 | 82 | 85 | 87 | 90 | 90 | 85 |

TABLE 1-continued

| | Example No. | | | | | | | | | |
|---|---|---|---|---|---|---|---|---|---|---|
| | 1 | 2 | 3 | 4 | 5 | 6 | 7 | 8 | 9 | 10 |
| Viscosity (cp) | 200 | 320 | 400 | 430 | 450 | 700 | 650 | 600 | 550 | 500 |

TABLE 2

| | Comparative Example No. | | | | | | | | | |
|---|---|---|---|---|---|---|---|---|---|---|
| | 1 | 2 | 3 | 4 | 5 | 6 | 7 | 8 | 9 | 10 |
| Composition (wt %): | | | | | | | | | | |
| Sodium N-lauroylaspartate | 20 | — | — | 10 | 10 | — | 8 | 12 | 10 | 8 |
| Lauryldimethylamine oxide | — | 20 | — | 10 | — | 10 | 6 | 6 | 2 | 4 |
| Sodium Dobanol 23(3Eϕ) sulfate | — | — | 20 | — | 10 | 10 | 6 | 2 | 8 | 8 |
| Performance Properties: | | | | | | | | | | |
| Foamability (ml) | 20 | 10 | 60 | 30 | 30 | 80 | 85 | 85 | 80 | 70 |
| Detergency (%) | 30 | 20 | 40 | 35 | 32 | 75 | 80 | 80 | 75 | 65 |
| Viscosity (cp) | slurry | 10 | 10 | clear gel | slurry | clear gel | 35000 | 20000 | 2000 | 3500 |

TABLE 3

| | Comparative Example No. | | | | | |
|---|---|---|---|---|---|---|
| | 1 | 2 | 3 | 4 | 5 | 6 |
| Composition (wt %): | | | | | | |
| Sodium N-lauroylglutamate | 18 | 12 | 10 | 12 | 15 | 14 |
| Lauryldimethylamine oxide | 1 | 2 | 4 | 4 | 4 | 2 |
| Sodium Dobanol 23(3Eϕ) sulfate | 1 | 6 | 6 | 4 | 1 | 4 |
| Performance Properties: | | | | | | |
| Foamability (ml) | 50 | 60 | 70 | 65 | 60 | 65 |
| Detergency (%) | 40 | 50 | 55 | 50 | 45 | 50 |
| Viscosity (cp) | 180 | 350 | 550 | 600 | 500 | 350 |

While the invention has been described in detail and with reference to specific embodiments thereof, it will be apparent to one skilled in the art that various changes and modifications can be made therein without departing from the spirit and scope thereof.

What is claimed is:

1. A fluid aqueous liquid detergent composition containing a detergent effective amount of a surfactant mixture containing (a) an N-acylaspartic acid or a salt thereof represented by formula (I):

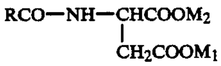

(I)

wherein R represents an alkyl or alkenly group having from 7 to 21 carbon atoms; and $M_1$ and $M_2$ each represents a hydrogen atom or a cation derived for Na, K, $NH_4$ or an alkanolamine, (b) a tertiary alkylamine oxide represented by formula (II):

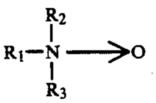

wherein $R_1$ represents an alkyl or alkenyl group having from 10 to 18 carbon atoms; and $R_2$ and $R_3$ each represents an alkyl group having from 1 to 3 carbon atoms, and (c) an alkyl ether sulfate represented by formula $$R_4-O-(CH_2CH_2O)_{p}-SO_3M_3 \quad \text{(III)}$$

wherein $R_4$ represents an alkyl or alkenyl group having from 7 to 20 carbon atoms; p represents an average number of moles of ethylene oxide added and is selected from an integer of from 1 to 5; and $M_3$ represents a cation derived from Na, K, $NH_4$ or an alkanolamine, the weight relative proportions of the components (a), (b), and (c) falling within the range indicated by a quadrate formed by four points (90,5,5), (75,20,5), (50,20,30), and (65,5,30) in a triangular coordinate constructed by placing the pure components (a), (b), and (c) at the vertices of a regular triangle.

2. The liquid detergent composition as claimed in claim 1 wherein said N-acylaspartic acid or a salt thereof is selected from the group consising of N-lauroylaspartic acid, N-myristoylaspartic acid, N-mytristoylaspartic acid, N-palmitoylaspartic acid, N-stearoylaspartic acid, and N-oleoylaspartic acid, and their salts.

3. The liquid detergent composition as claimed in claim 1 wherein said tertiary alkylamine oxide is selected from the group consising of lauryldimethylamine oxide, myristyldimethylamine oxide, cetyldimethylamine oxide, lauryl-2-hydroxyethylamine, laurylmethylethylamine oxide, lauryldiethylamine oxide, myristyldiethylamine oxide, oleyldimethylamine oxide, oleyldiethylamine oxide, myristylethylpropylamine oxide, lauryldipropylamine oxide, myristyldipropylamine oxide, cetyldipropylamine oxide, cetylmethylpropylamine oxide, and cocoalkyldimethylamine oxide.

4. The liquid detergent composition as claimed in claim 1 wherein $R_4$ represents an alkyl or alkyenyl group having 12 or 13 carbon atoms; $\bar{p}$ is 3; and $M_3$ represents a cation derived from Na.

* * * * *